(12) United States Patent
Joseph et al.

(10) Patent No.: US 11,504,201 B2
(45) Date of Patent: Nov. 22, 2022

(54) HAPTIC TOUCH FEEDBACK SURGICAL DEVICE FOR PALPATING TISSUE

(71) Applicant: COVIDIEN LP, Mansfield, MA (US)

(72) Inventors: Daniel A. Joseph, Golden, CO (US); John A. Hammerland, III, Arvada, CO (US); Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 848 days.

(21) Appl. No.: 16/424,211

(22) Filed: May 28, 2019

(65) Prior Publication Data

US 2019/0365493 A1    Dec. 5, 2019

Related U.S. Application Data

(60) Provisional application No. 62/820,321, filed on Mar. 19, 2019, provisional application No. 62/678,505, filed on May 31, 2018.

(51) Int. Cl.
*A61B 34/00* (2016.01)
*A61B 34/35* (2016.01)
*A61B 90/00* (2016.01)
*A61B 34/20* (2016.01)
(Continued)

(52) U.S. Cl.
CPC .............. *A61B 34/76* (2016.02); *A61B 34/20* (2016.02); *A61B 34/25* (2016.02); *A61B 34/35* (2016.02); *A61B 90/06* (2016.02); *A61B 90/361* (2016.02); *G06F 3/014* (2013.01); *A61B 90/37* (2016.02); *A61B 2034/2055* (2016.02); *A61B 2034/302* (2016.02); *A61B 2034/305* (2016.02); *A61B 2090/064* (2016.02); *A61B 2090/065* (2016.02);
(Continued)

(58) Field of Classification Search
None
See application file for complete search history.

(56) References Cited

U.S. PATENT DOCUMENTS 5,029,478 A * 7/1991 Wamstad .............. G01L 19/142
                                                              73/726
6,377,011 B1   4/2002 Ben-Ur
7,289,106 B2  10/2007 Bailey et al.
(Continued)

FOREIGN PATENT DOCUMENTS

WO      2016025132 A1    2/2016

*Primary Examiner* — Vicky A Johnson
(74) *Attorney, Agent, or Firm* — Carter, DeLuca & Farrell LLP

(57) ABSTRACT

A surgical device for providing haptic feedback includes a housing having a cavity defined therein configured to receive a finger of a user and an elongated shaft configured to extend through the housing and into the cavity and configured to support a spring thereon and a pressure contact. A fluid-filled sensor is included that has a plurality of tubes configured to extend from the cavity, each tube includes a fluid-filled bladder at both ends thereof joined by a fluid channel therebetween. Each tube is configured to contain a fluid therein such that when a user's finger is engaged between the fluid-filled bladder at the proximal end of the tubes and the pressure contact, changes in pressure in the fluid-filled bladders at a distal end of the tubes is correspondingly registered in the fluid-filled bladders at the proximal end of the tubes providing haptic feedback to the user.

24 Claims, 8 Drawing Sheets

(51) Int. Cl.
*G06F 3/01* (2006.01)
*A61B 34/30* (2016.01)

(52) U.S. Cl.
CPC ...... *A61B 2562/0247* (2013.01); *G06F 3/016* (2013.01)

(56) References Cited

U.S. PATENT DOCUMENTS

| | | |
|---|---|---|
| 7,342,573 B2 | 3/2008 | Ryynanen |
| 7,563,233 B2 | 7/2009 | Kuth |
| 7,579,758 B2 | 8/2009 | Maruyama et al. |
| 7,663,604 B2 | 2/2010 | Maruyama et al. |
| 8,063,893 B2 | 11/2011 | Rosenberg et al. |
| 8,174,495 B2 | 5/2012 | Takashima et al. |
| 8,638,308 B2 | 1/2014 | Cunningham et al. |
| 8,659,536 B2 | 2/2014 | Park et al. |
| 8,942,828 B1 | 1/2015 | Schecter |
| 9,563,266 B2 | 2/2017 | Banerjee et al. |
| 9,671,865 B2 | 6/2017 | Modarres et al. |
| 9,785,238 B2 | 10/2017 | Birnbaum et al. |
| 9,823,833 B2 | 11/2017 | Grant et al. |
| 9,829,977 B2 | 11/2017 | Heubel et al. |
| 9,857,872 B2 | 1/2018 | Terlizzi et al. |
| 9,870,053 B2 | 1/2018 | Modarres et al. |
| 2005/0245910 A1* | 11/2005 | Wright ............... A61F 9/00745 606/1 |
| 2006/0209037 A1 | 9/2006 | Wang et al. |
| 2007/0096666 A1* | 5/2007 | Ippisch ............... A61B 17/1626 318/71 |
| 2008/0218488 A1 | 9/2008 | Yang et al. |
| 2010/0283731 A1 | 11/2010 | Grant et al. |
| 2011/0178508 A1* | 7/2011 | Ullrich ............... A61B 34/70 606/1 |
| 2012/0116416 A1 | 5/2012 | Neff et al. |
| 2012/0174680 A1* | 7/2012 | Wade ............... G01L 19/0038 73/721 |
| 2013/0321262 A1 | 12/2013 | Schecter |
| 2014/0002427 A1 | 1/2014 | Yeo et al. |
| 2014/0375580 A1 | 12/2014 | Peshkin et al. |
| 2016/0320901 A1 | 11/2016 | Son et al. |
| 2016/0357342 A1 | 12/2016 | Olley et al. |
| 2017/0181634 A1 | 6/2017 | Burke et al. |
| 2017/0181808 A1 | 6/2017 | Panescu et al. |

\* cited by examiner

HAPTIC TOUCH FEEDBACK SURGICAL DEVICE FOR PALPATING TISSUE

CROSS REFERENCE TO RELATED APPLICATION

The present application claims the benefit of and priority to U.S. Provisional Application No. 62/678,505, filed on May 31, 2018 and U.S. Provisional Application No. 62/820,321, filed on Mar. 19, 2019. The entire contents of each the above applications are hereby incorporated by reference herein.

TECHNICAL FIELD

The present disclosure relates to laparoscopic devices and procedures and, more particularly, to devices and methods for providing external haptic feedback to surgeons of internal bodily structures.

BACKGROUND

Various types of laparoscopic surgery involve making one or more incisions within a patient's tissue (e.g., abdomen) to allow laparoscopic instruments and cameras access to one or more internal organs for excision or treatment. Typically, the various actuators and controls for the instrument remain external to the body cavity allowing the surgeon to manipulate the treatment portion of the instrument in vivo. With some surgeries it is often difficult to assess if a laparoscopic surgical technique can be substituted for an open surgical technique due to many factors including the difficulty of a surgeon to feel the tissue treatment area or palpate tissue prior to operating. As a result, open techniques are traditionally employed over laparoscopic techniques in these instances.

SUMMARY

In accordance with an aspect of the present disclosure, a surgical device for providing haptic feedback includes a housing having a cavity defined therein configured to receive a finger of a user. An elongated shaft is configured to extend through one end of the housing and into the cavity and is configured to support a biasing member thereon and a pressure contact at a distal end thereof. A fluid-filled sensor is included having a plurality of elongated tubes configured to extend from the cavity and through an opposite end of the housing. Each tube of the plurality of tubes includes a fluid-filled bladder at both ends thereof joined by a fluid channel defined therebetween. Each tube of the plurality of tubes is configured to contain a fluid therein such that when a user's finger is engaged within the cavity against the fluid-filled bladders at a proximal end of the plurality of tubes and between the pressure contact under the bias of the biasing member, changes in pressure in the fluid-filled bladders at a distal end of the plurality of tubes is correspondingly registered in the fluid-filled bladders at the proximal end of the plurality of tubes providing haptic feedback to the user.

In aspects according to the present disclosure, each fluid-filled bladder includes an inner periphery configured to securely engage one of the plurality of tubes and an outer periphery configured to engage the housing. In other aspects, a stop is included and is configured to contain the distal ends of the plurality of tubes. In still other aspects according to the present disclosure, each of the fluid-filled bladders includes an outer periphery having a geometric configuration and the stop includes an inner periphery having a complementary geometric configuration to securely engage the plurality of fluid-filled bladders therein.

In aspects according to the present disclosure, the housing includes one or more finger rests for stabilizing the surgical device during use. The finger rest(s) may be C-shaped. In aspects, the housing includes two C-shaped finger rests on opposing ends thereof that are configured to support the fingers that are adjacent the finger disposed within the cavity.

In yet other aspects according to the present disclosure, one or more of the fluid-filled bladders is rounded. In aspects, the fluid-filled bladders at the proximal end of the plurality of tubes include a first geometric profile and the fluid-filled bladders at the distal end of the plurality of tubes include a second geometric profile.

In still other aspects, the fluid may be pressurized. In aspects, the fluid-filled bladders are configured such that the changes in pressure between the fluid-filled bladders at the proximal and distal ends of the plurality of tubes allows the user to sense changes in tissue hardness, tissue type and tissue contour, etc.

In yet other aspects, the fluid-filled bladders are made from a resilient material selected from the group consisting of rubber, silicone, urethane, thermoplastic elastomers, etc.

In accordance with another aspect of the present disclosure, the present disclosure includes a surgical device for providing haptic feedback to a user having a housing including a cavity defined therein configured to receive a first finger of a user and a pair of opposing finger rests on either side of the housing configured to support the adjacent fingers of the user. An elongated shaft is configured to extend through one end of the housing and into the cavity and configured to support a biasing member thereon and a pressure contact at a distal end thereof. A fluid-filled sensor having a plurality of elongated tubes is configured to extend from the cavity and through an opposite end of the housing. Each tube of the plurality of tubes includes a resilient fluid-filled bladder at both ends thereof joined by a fluid channel defined therebetween. Each tube of the plurality of tubes is configured to contain a fluid therein such that when the user's first finger is engaged within the cavity against the resilient fluid-filled bladders at a proximal end of the plurality of tubes and between the pressure contact under the bias of the biasing member, changes in pressure in the resilient fluid-filled bladders at a distal end of the plurality of tubes is correspondingly registered in the resilient fluid-filled bladders at the proximal end of the plurality of tubes providing haptic feedback to the user.

In accordance with another aspect of the present disclosure, a surgical device for providing haptic feedback includes a housing having a cavity defined therein configured to receive a finger of a user. An elongated shaft is included having a proximal portion configured to extend through one end of the housing and into the cavity and configured to support a sensor pad thereon. The elongated shaft also includes a distal portion configured to support a sensor having an array of fluid-filled diaphragms associated therewith. The sensor is configured to detect changes in pressure within the fluid-filled diaphragms and communicate the changes in pressure to the sensor pad which, in turn, provides feedback to the user.

In aspects according to the present disclosure, the sensor is a capacitive sensor. In other aspects, the fluid-filled diaphragm includes hydraulic fluid. In still other aspects according to the present disclosure the sensor pad includes an array of haptic-like sensors disposed thereon.

In aspects according to the present disclosure, the cavity is defined by a pair of opposing C-shaped flanges. In yet other aspects, the sensor pad includes an array of haptic-like sensors disposed on an inner facing surface of one of the C-shaped flanges.

In accordance with another aspect of the present disclosure, a surgical device for providing haptic feedback includes a housing having a cavity defined therein configured to receive a finger of a user. An elongated shaft is included that has a proximal portion configured to extend through one end of the housing and into the cavity and configured to support a sensor pad thereon The elongated shaft also includes a distal portion configured to support an array of fluid-filled diaphragms each including a pressure sensor associated therewith. Each pressure sensor is configured to detect changes in pressure within a respective fluid-filled diaphragm and communicate the changes in pressure to the sensor pad which, in turn, provides feedback to the user.

In aspects according to the present disclosure, the sensor is a capacitive sensor. In other aspects, the fluid-filled diaphragm includes hydraulic fluid. In still other aspects according to the present disclosure the sensor pad includes an array of haptic-like sensors disposed thereon.

In aspects according to the present disclosure, the cavity is defined by a pair of opposing C-shaped flanges. In yet other aspects, the sensor pad includes an array of haptic-like sensors disposed on an inner facing surface of one of the C-shaped flanges.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1A:
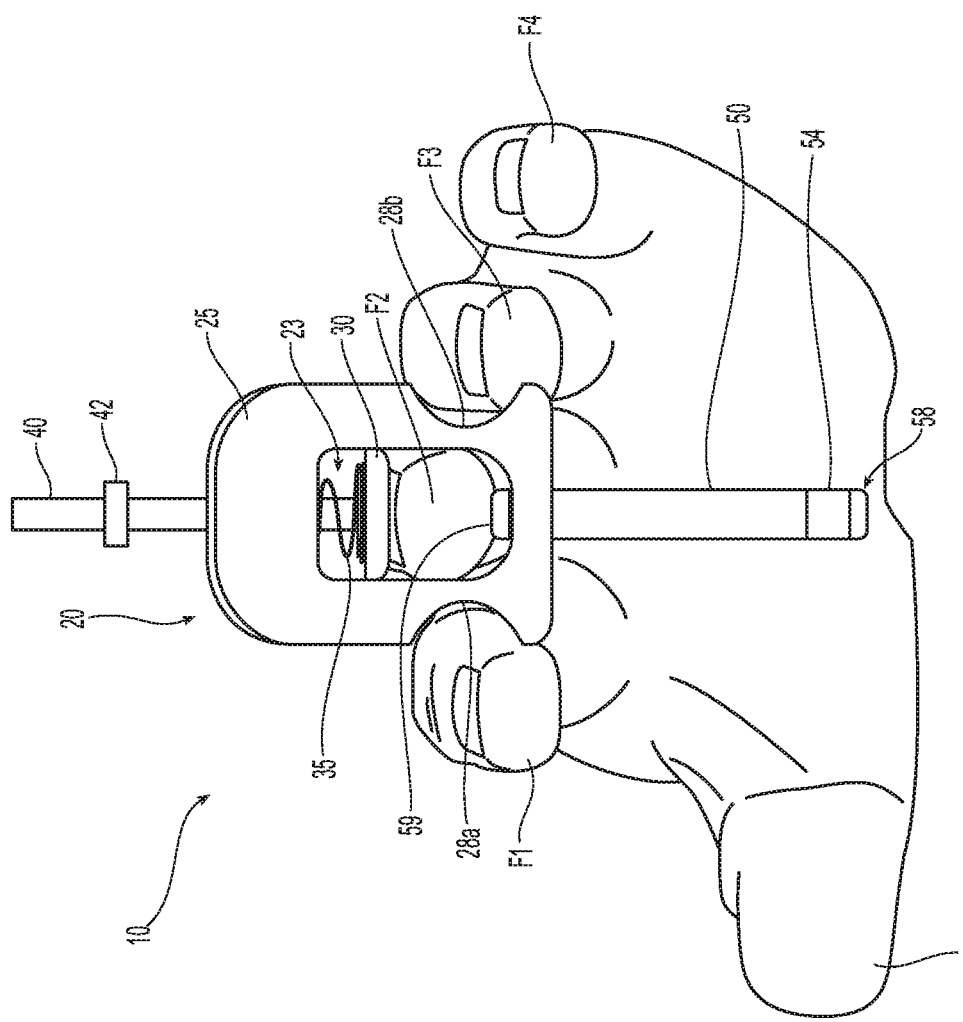
FIG. 1A is a front view of a surgical device for palpating tissue in accordance with the principles of the present disclosure.

Embodiments of the present surgical devices used for providing haptic feedback are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel.

In the following description, well-known functions or constructions are not described in detail to avoid obscuring the present disclosure in unnecessary detail.

Figure 1B:
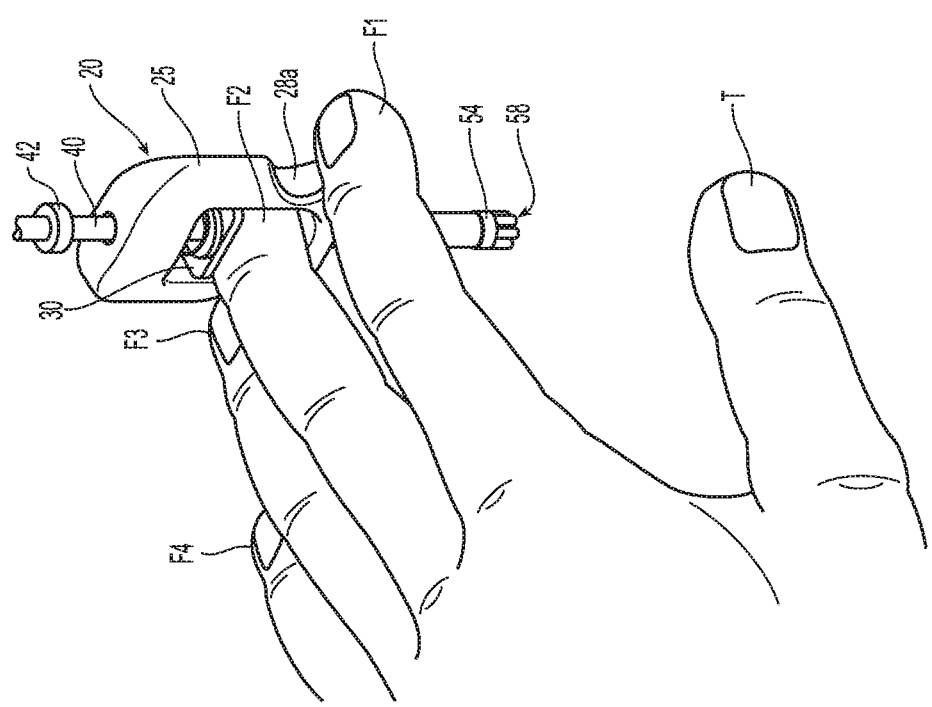
FIG. 1B is rear, perspective view of the surgical device of FIG. 1A.
Figure 2:
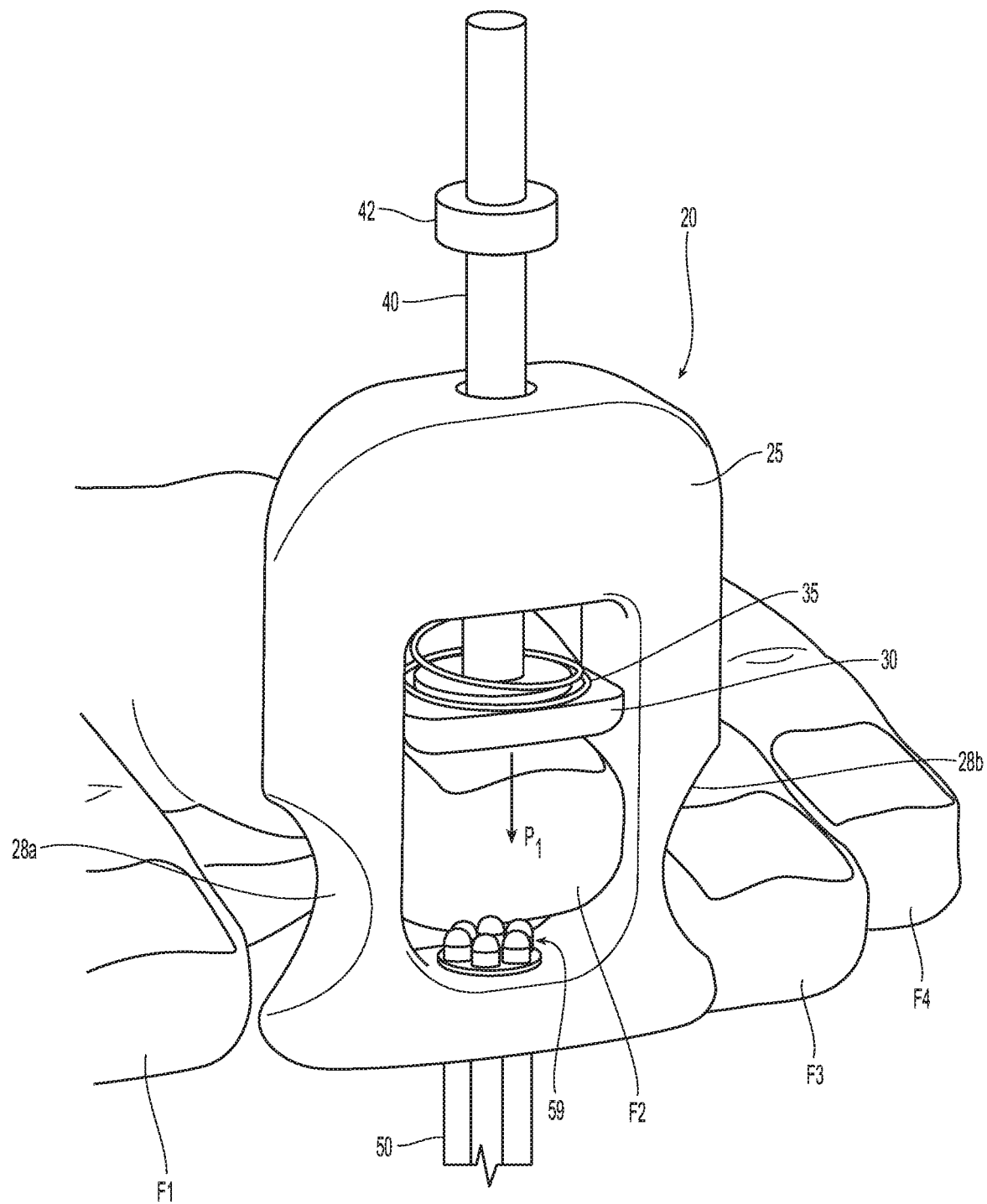
FIG. 2 is an enlarged, front perspective view of the surgical device of FIG. 1A.

Turning now to FIGS. 1A-1B, one embodiment of a surgical device for providing haptic feedback is shown and is generally referred to as surgical device 10. Surgical device 10 includes a housing 20 having a cavity 23 defined therein configured to receive an elongated shaft 40 for reciprocation within the cavity 23. Housing 20 includes a pair of opposing C-shaped finger rests 28a and 28b defined on either side thereof configured to support the fingers, e.g., fingers F1 and F3, of a user on either side thereof. Cavity 23 is sized to receive a finger, e.g., finger F2, therein such that the three fingers, F1, F2 and F3 support and stabilize the surgical device 10 for use. Any fingers on a user's hand may be utilized. Housing 20 is also configured to receive a fluid-filled sensor 50 within an aperture 59 defined in cavity 23 at a distal-most portion thereof (FIG. 2). Fluid-filled sensor 50 may include and array of fluid-filled tubes 51a-51g having bladders 58a-58g and 59a-59g at either end thereof made from various types of resilient materials that readily react, e.g., deform, with changes in pressure. The fluid-filled bladders 51a-51g may be made from any type of resilient material rubber, silicone, urethane, thermoplastic elastomers, etc.

Figure 4:
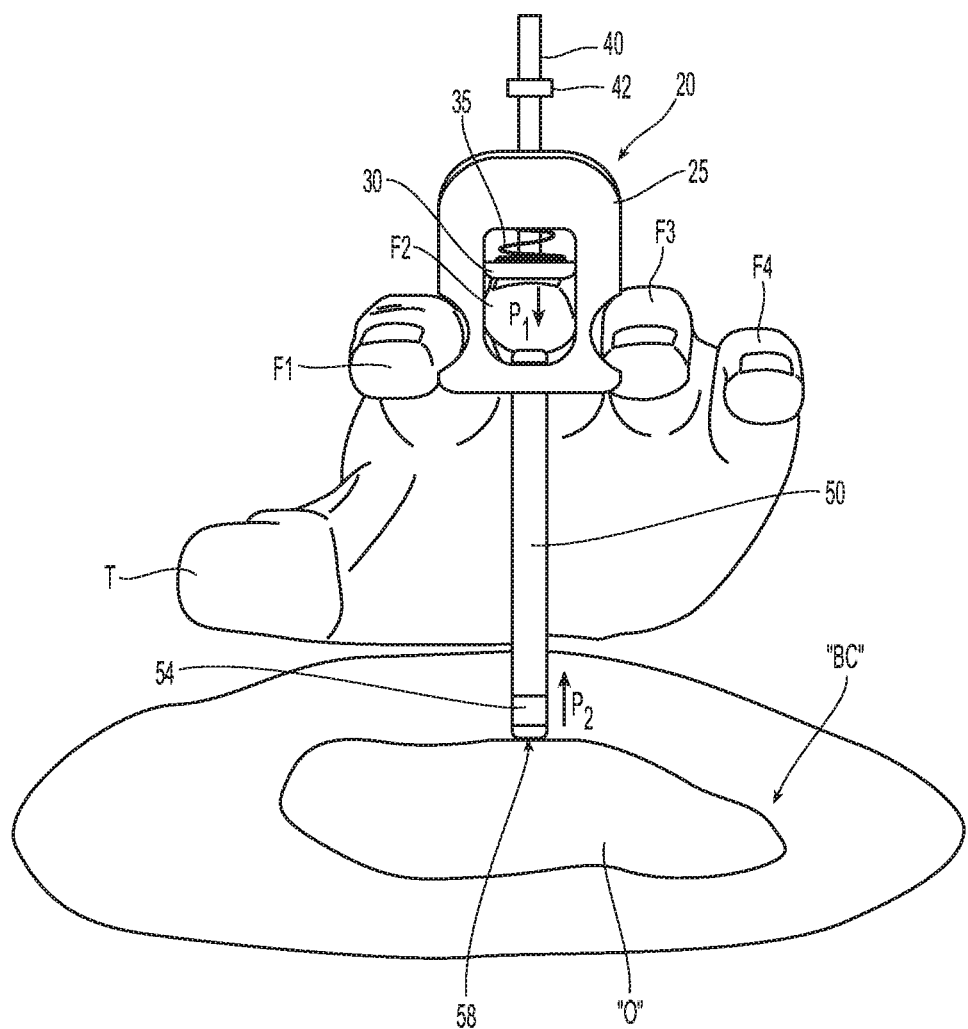
FIG. 4 is a front view of the surgical device according to the present disclosure shown in vivo.

Elongated shaft 40 supports a stop 42 at a proximal end thereof and a pressure contact 30 at a distal end thereof. Stop 42 is disposed on the outside of housing 20 and pressure contact 30 is disposed within cavity 23. Pressure contact 30 is configured to support one side, e.g., the finger nail side, of finger F2, while the opposing side of finger F2, e.g., finger print side, rests atop the fluid-filled sensor 50. A biasing member, e.g., spring 35, biases the pressure contact 30 with a pressure "P1" in a direction towards a distal-most portion of cavity 23 and acts to provide pressure against finger F2 when seated within cavity 23. As explained in further detail below, as the surgical device 10 is used, an opposing pressure P2 from the fluid-filled sensor 50 acts against the pressure P1 allowing the surgeon to feel or palpate the differences in pressure between the ends of the sensor 50 and therefore the differences in tissue contour and hardness remotely, e.g., within an internal body cavity "BC" (FIG. 4). The sensor 50 is not limited in length nor does it need to be straight and inflexible.

Figure 3A:
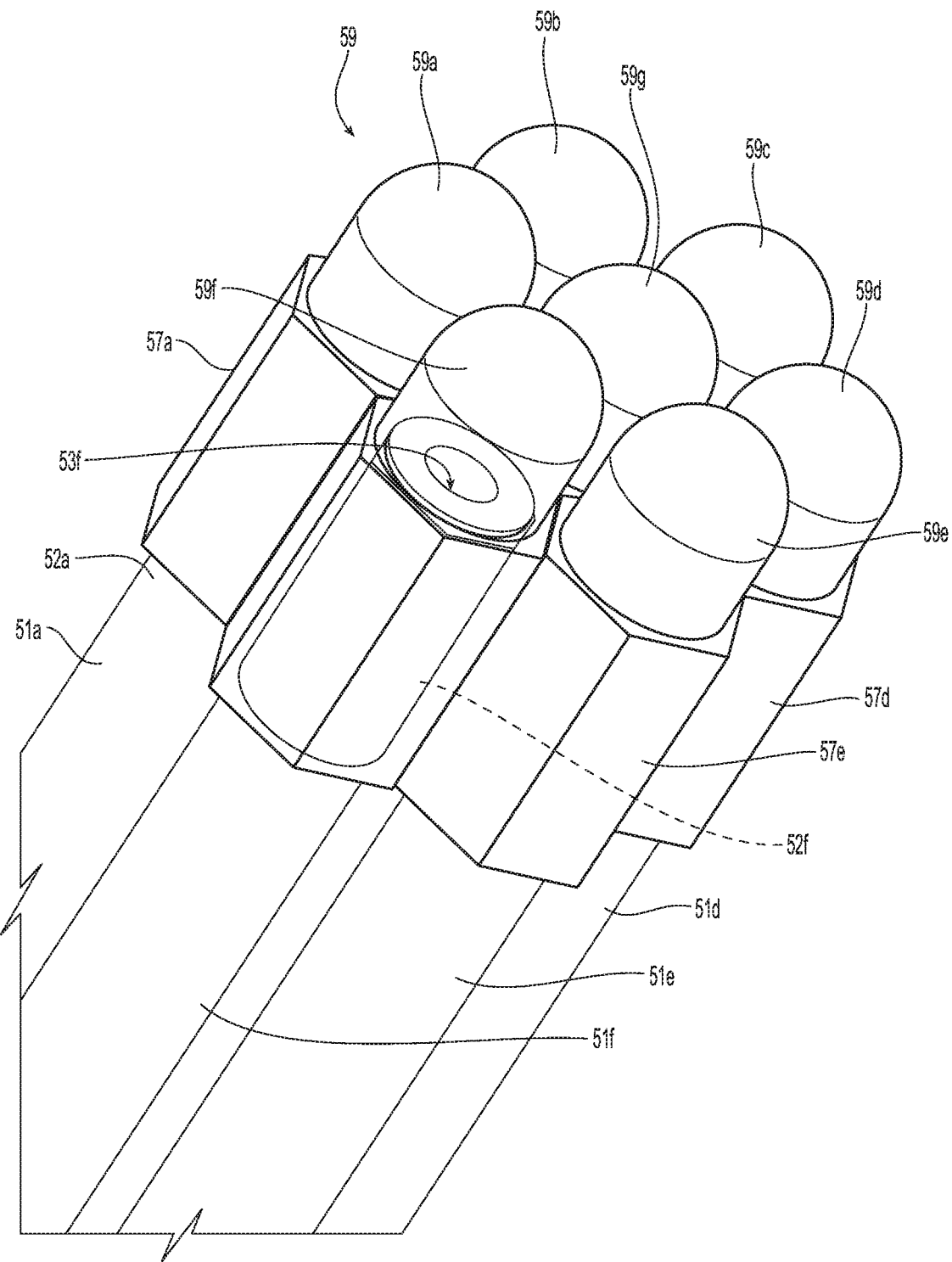
FIG. 3A is an enlarged, perspective view of a proximal end portion of an array of fluid-filled sensing tubes of the surgical device of FIG. 1A.
Figure 3B:
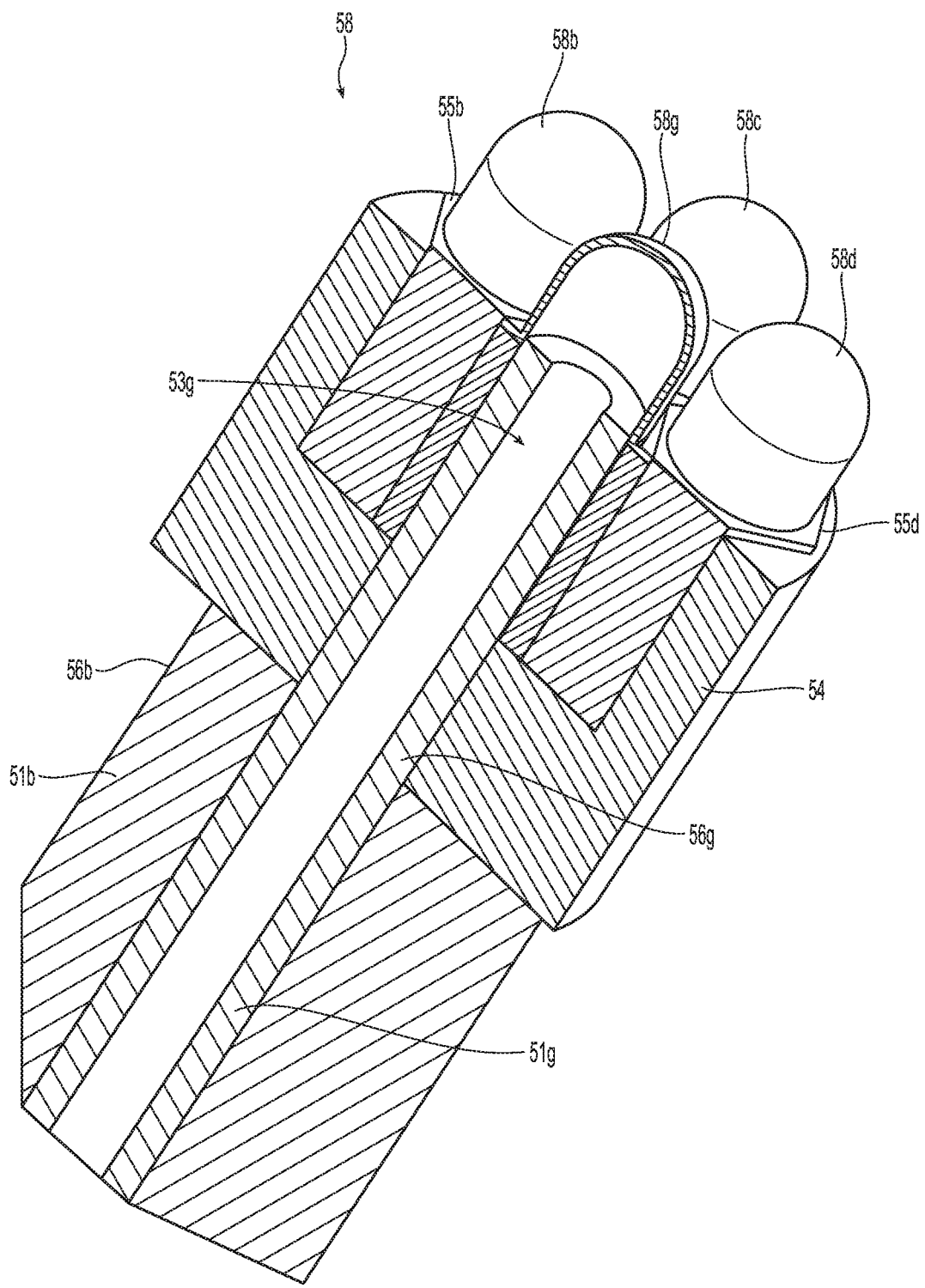
FIG. 3B is an enlarged, perspective, cut-away view of a distal end portion of the array of fluid-filled sensing tubes of the surgical device of FIG. 1A.

FIGS. 2-3B show enlarged views of various aspects of the surgical device 10 and more clearly depicts the fluid-filled sensors 50. As mentioned above, the fluid-filled sensor 50 includes a plurality of tubes 51a-51g arranged in a generally circular manner (array) each having respective proximal ends 52a-52g (FIG. 3A) and distal ends 56a-56g (FIG. 3B).

A corresponding plurality of fluid bladders 59a-59g are secured at the proximal ends 52a-52g of each tube 51a-51g via a corresponding cap 57a-57g. The interior of each cap 57a-57g is configured to securely engage each fluid bladder 59a-59g to the respective end of each tube 51a-51g and the outer periphery of each cap 57a-57g is configured to secure the fluid-filled sensor 50 within the distal end of cavity 23 (FIGS. 1A and 2).

The distal ends 56a-56g of each of the plurality of tubes 51a-51g each include a similar style cap 55a-55g that secures a similar style fluid bladder 58a-58g thereon. Other style caps 55a-55g (or 57a-57g) are contemplated depending upon a particular purpose. Bladders, 58a-58g, 59a-59g are shown generally rounded, however, bladders 58a-58g, 59a-59g may be any other configuration, e.g., pointed, flat, indented, etc., to provide for a particular surgical need, e.g., to provide an enhanced feel under some circumstances.

A stop 54 secures the plurality of caps 55a-55g at the distal ends 56a-56g of tubes 51a-51g in fluid tight arrangement such that the caps 55a-55g remain in fixed relation relative to one another. As explained in more detail below, the stop 54 along with the securing of the proximal ends 52a-52g of the tubes 51a-51g within the cavity 23 assures that there is no relative movement between the respective tubes 51a-51g and movement is restricted to the relative pressure differential in the fluid-filled bladders 58a-58g and 59a-59g.

Each tube, e.g., 51f, of the plurality of tubes 51a-51g, includes a channel, e.g., channel 53f, defined therein that extends from the proximal end 52f to the distal end 56f (56g shown) thereof. Channel 53f is configured to contain a fluid (not shown) therein. The fluid may be pressurized depending upon a particular purpose or to achieve a particular result. The fluid extends into the fluid-filled bladders, e.g., bladders 58g, 59g, on both the proximal 52f and distal ends 56f, respectively.

In use, a surgeon grips the surgical device 10 in the manner shown in FIGS. 1A-2 such that the middle finger F2 is disposed within cavity 23 between the fluid-filled bladders 59a-59g and the pressure contact 30. Although shown as the middle finger, any finger may be utilized. Spring 35 applies a bias to the finger F2 against the fluid-filled bladders 59a-59g. Fingers F1 and F3 are disposed within C-shaped finger rests 28a and 28b and provide stability to the surgical device during use.

The surgeon makes a small incision in the patient and inserts the distal end 58 of the surgical device 10 and the stop 54 within the incision (or within a trocar (not shown)) and into the incision (FIG. 4). The surgeon then orients the surgical device 10 within the surgical body cavity "BC" to engage an organ "O" or other bodily structure. The surgeon applies slight pressure and moves the distal end 58 of the surgical device 10 such that the plurality of fluid-filled bladders 58a-58g moves across the organ "O". As the plurality of fluid-filled bladders 58a-58g moves across the organ "O" the pressure differential (between pressure P1 and P2) of each fluid-filled bladder, e.g., bladder 58a, is felt by the surgeon on the opposite end of tube 52a with the corresponding fluid-filled bladder, e.g., 59a at the proximal end 59.

The bias of the spring 35 keeps the finger F2 in contact with the fluid-filled bladders 59a-59g such that the surgeon can feel the changes in pressure P2 as the distal end 58 moves across the organ "O". In other words, the tip of the surgeon's finger F2 moves slightly up and down against the spring 35 as it rides atop shaft 40 with the variations in pressure as the distal end 58 moves across the organ "O".

This enables the surgeon to assess various tissue types and densities as the surgical device 10 moves across the organ "O", e.g., dense tissue versus soft tissue, lumps (tumors) versus smooth (healthy) tissue, different tissue types, etc.

An opposable structure may be used to hold tissue against the sensor end within the body. This opposable structure can mimic the function of grabbing and squeezing tissue between the user's fingers. This squeezing operation may facilitate surgical actions laparoscopically that previously were only able to be performed with open surgical procedures; physical hepatic parenchyma inspection for the change in hardness from healthy soft tissue to hard tumors or liver cirrhosis.

Turning now to FIGS. 5A-6B, another embodiment of a surgical device for providing haptic feedback is shown and is generally referred to as surgical device 500. Surgical device 500 includes a housing 520 having a cavity 523 defined therein configured to receive an elongated shaft 540 within the cavity 523 (See FIG. 6A). Cavity 523 is defined by a pair of opposing C-shaped flanges 528a and 528b configured to receive a finger F1 of a user therein. Cavity 523 is sized to receive finger F1 in a friction fit (or otherwise secure) manner to both support and stabilize the surgical device 500 for use. Housing 520 is configured to receive a sensor pad 560 disposed on an inner surface of flange 528b. Sensor pad 560 includes an array of haptic-like sensors 560a-560d that are configured to provide feedback to the user during use as explained in more detail below. The array of haptic-like sensors 560a-560d may include any number of diaphragms, piezo electric activators, and/or various types of signal processors.

Figure 5A:
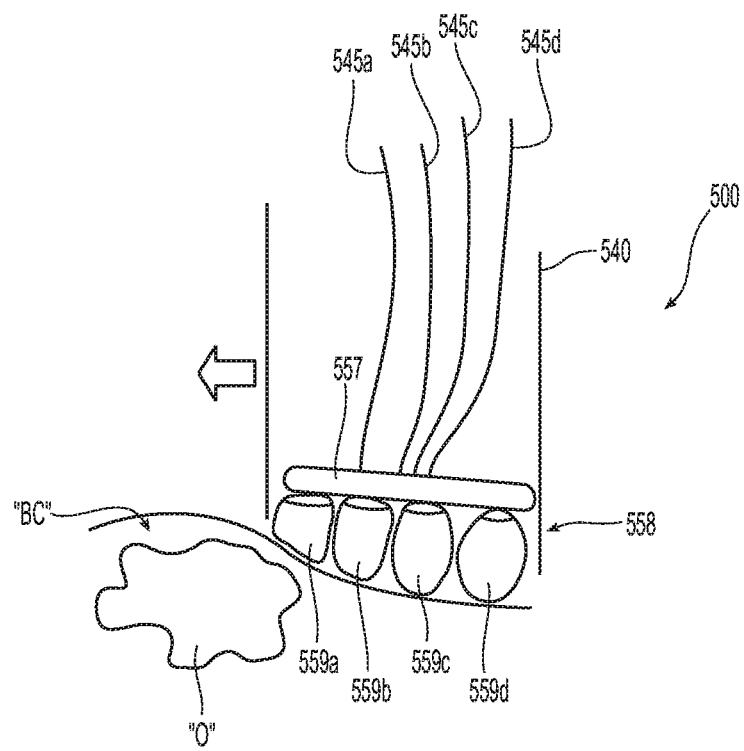
FIG. 5A is an enlarged, schematic view of a distal portion of another embodiment of a surgical device for palpating tissue in accordance with the principles of the present disclosure including a capacitive sensor.

Elongated shaft 540 supports a capacitive sensor 557 (or the like) at a distal portion thereof which, in turn, supports an array of hydraulic diaphragms 559a-559d that are configured to engage the tissue (See FIG. 5A). Any number of hydraulic diaphragms 559a-559d is envisioned. Similar to the embodiments described above with respect to FIGS. 1-4, each diaphragm, e.g., diaphragm 559a, is configured to displace fluid (hydraulic fluid) based upon the tissue the diaphragm 559a is contacting. Capacitive sensor 557 transmits the changes in pressure to the sensor pad 560 to provide feedback to the user.

Figure 5B:
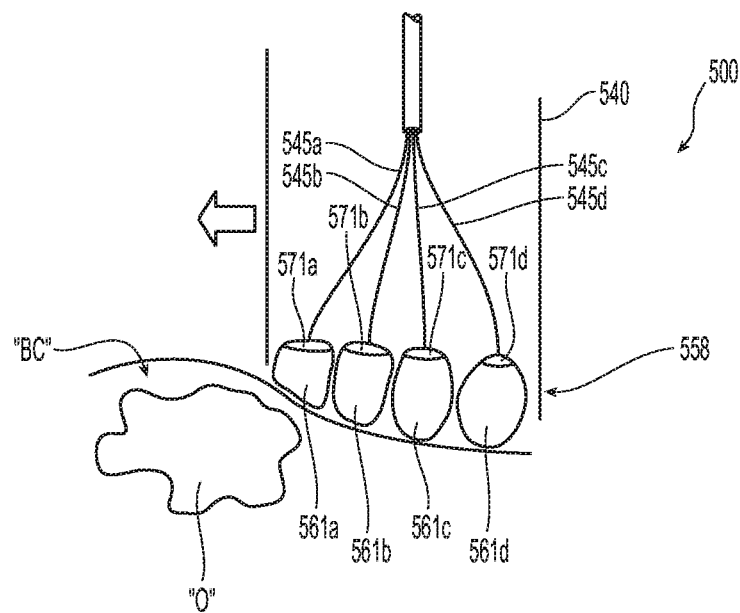
FIG. 5B is an enlarged, schematic view of a distal portion of another embodiment of a surgical device for palpating tissue in accordance with the principles of the present disclosure including a plurality of conductive spheres and corresponding pressure sensors.
Figure 6A:
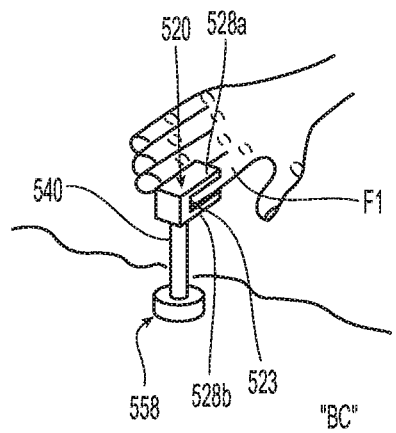
FIG. 6A is a schematic view of the surgical device of FIG. 5A shown in use.
Figure 6B:
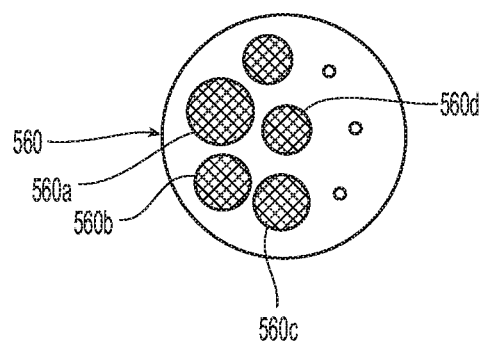
FIG. 6B is an enlarged top view of a sensor pad for use with the embodiment of FIG. 5A.

Alternatively, flexible conductive spheres 561a-561d may be utilized for this same purpose (See FIG. 5B). In this instance, each flexible conductive sphere 561a-561d includes a respective pressure sensor 571a-571d that is configured to sense changes in pressure and convert these changes in pressure to electrical signals. The electrical signals are, in turn, sent via wires 545a-545d (or by other communication means) to haptic-like sensors 560a-560d to be converted into various types of mechanical feedback.

The electrical signals from wires 545a-545d may be configured to drive a positive displacement pump (e.g., piston and cylinder which acts as the haptic-like sensors 560a-560d) for each diaphragm 559a-559d (FIG. 5A) or flexible conductive sphere 561a-561d (FIG. 5B) to move a related proximal diaphragm (not shown) in a similar array that the doctor then can place his hand or finger upon to get the feeling of the tissue. The electrical signals may be configured to drive a piezo electric activator (which acts as the haptic-like sensor 560a-560d) in a similar array to the array of diaphragms 559a-559d or flexible conductive spheres 561a-561d on the distal portion of shaft 540 such that the doctor can place his/her finger upon the proximal end of the shaft 540 to get the feeling of the tissue. A signal processor (not shown) may be utilized to determine the overall feel of the tissue and report the information as processed data to the sensor pad 560, e.g., hard, soft, containing density differentials, bumpy, etc.

The diaphragms 559a-559d or flexible conductive spheres 561a-561d and the sensor pad 560 may be different configurations depending upon a particular purpose. In other words, the array of diaphragms 559a-559d or flexible conductive spheres 561a-561d does not have to have the same layout as the haptic-like sensors 560a-560d which can enhance feedback or ease of manufacturing. For example, more haptic-like sensors 560a-560d could be utilized to provide a sharper or more focused feel to overcome any losses due to use through a surgical glove or less haptic-like sensors to accommodate robotic use without a surgical glove The general concepts discussed herein can be installed on opposing surfaces of a pair of jaw members of a forceps or grasping tool (not shown) to allow pinching of tissue between a user's finger and thumb. The user end would have similar array on a pincer type user interface wherein the feedback would be on one of the contact pads for the user's finger or thumb.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical device for providing haptic feedback, comprising:
   a housing having a cavity defined therein configured to receive a finger of a user;
   an elongated shaft configured to extend through one end of the housing and into the cavity and configured to support a biasing member thereon and a pressure contact at a distal end thereof; and
   a fluid-filled sensor including a plurality of elongated tubes configured to extend from the cavity and through an opposite end of the housing, each tube of the plurality of tubes including a fluid-filled bladder at both ends thereof joined by a fluid channel defined therebetween, each tube of the plurality of tubes configured to contain a fluid therein, wherein when a user's finger is engaged within the cavity against the fluid-filled bladders at a proximal end of the plurality of tubes and between the pressure contact under the bias of the biasing member, changes in pressure in the fluid-filled bladders at a distal end of the plurality of tubes is correspondingly registered in the fluid-filled bladders at the proximal end of the plurality of tubes providing haptic feedback to the user.

2. The surgical device for providing haptic feedback according to claim 1 wherein each fluid-filled bladder includes an inner periphery configured to securely engage one of the plurality of tubes and an outer periphery configured to engage the housing.

3. The surgical device for providing haptic feedback according to claim 1 further comprising a stop configured to contain the distal ends of the plurality of tubes.

4. The surgical device for providing haptic feedback according to claim 3 wherein each of the fluid-filled bladders includes an outer periphery having a geometric configuration and the stop includes an inner periphery having a complementary geometric configuration to securely engage the plurality of fluid-filled bladders therein.

5. The surgical device for providing haptic feedback according to claim 1 wherein the housing includes at least one finger rest for stabilizing the surgical device during use.

6. The surgical device for providing haptic feedback according to claim 5 wherein the at least one finger rest is C-shaped.

7. The surgical device for providing haptic feedback according to claim 5 wherein the housing includes two C-shaped finger rests on opposing ends thereof for supporting the fingers that are adjacent the finger disposed within the cavity.

8. The surgical device for providing haptic feedback according to claim 1 wherein at least one of the fluid-filled bladders is rounded.

9. The surgical device for providing haptic feedback according to claim 1 wherein the fluid-filled bladders at the proximal end of the plurality of tubes include a first geometric profile and the fluid-filled bladders at the distal end of the plurality of tubes include a second geometric profile.

10. The surgical device for providing haptic feedback according to claim 1 wherein the fluid in the plurality of tubes is pressurized.

11. The surgical device for providing haptic feedback according to claim 1 wherein the fluid-filled bladders are configured such that the changes in pressure between the fluid-filled bladders at the proximal and distal ends of the plurality of tubes allows the user to sense changes in tissue hardness, tissue type and tissue contour.

12. The surgical device for providing haptic feedback according to claim 11 wherein the fluid-filled bladders are made from a resilient material selected from the group consisting of rubber, silicone, urethane, and thermoplastic elastomers.

13. A surgical device for providing haptic feedback, comprising:
    a housing having a cavity defined therein configured to receive a first finger of a user and a pair of opposing finger rests on either side of the housing configured to support the adjacent fingers of the user;
    an elongated shaft configured to extend through one end of the housing and into the cavity and configured to support a biasing member thereon and a pressure contact at a distal end thereof; and
    a fluid-filled sensor including a plurality of elongated tubes configured to extend from the cavity and through an opposite end of the housing, each tube of the plurality of tubes including a resilient fluid-filled bladder at both ends thereof joined by a fluid channel defined therebetween, each tube of the plurality of tubes configured to contain a fluid therein, wherein when the user's first finger is engaged within the cavity against the resilient fluid-filled bladders at a proximal end of the plurality of tubes and between the pressure contact under the bias of the biasing member, changes in pressure in the resilient fluid-filled bladders at a distal end of the plurality of tubes is correspondingly registered in the resilient fluid-filled bladders at the proximal end of the plurality of tubes providing haptic feedback to the user.

14. A surgical device for providing haptic feedback, comprising:
    a housing having a cavity defined therein configured to receive a finger of a user;
    an elongated shaft including a proximal portion configured to extend through one end of the housing and into the cavity and configured to support a sensor pad thereon, the elongated shaft also including a distal portion configured to support a sensor including an array of fluid-filled diaphragms associated therewith, the sensor configured to detect changes in pressure within the fluid-filled diaphragms and communicate the changes in pressure to the sensor pad which, in turn, provides feedback to the user.

15. The surgical device for providing haptic feedback according to claim 14 wherein the sensor is a capacitive sensor.

16. The surgical device for providing haptic feedback according to claim 14 wherein the fluid-filled diaphragm includes hydraulic fluid.

17. The surgical device for providing haptic feedback according to claim 14 wherein the sensor pad includes an array of haptic-like sensors disposed thereon.

18. The surgical device for providing haptic feedback according to claim 14 wherein the cavity is defined by a pair of opposing C-shaped flanges.

19. The surgical device for providing haptic feedback according to claim 18 wherein the sensor pad includes an array of haptic-like sensors disposed on an inner facing surface of one of the C-shaped flanges.

20. A surgical device for providing haptic feedback, comprising:
    a housing having a cavity defined therein configured to receive a finger of a user;
    an elongated shaft including a proximal portion configured to extend through one end of the housing and into the cavity and configured to support a sensor pad thereon, the elongated shaft also including a distal portion configured to support an array of fluid-filled diaphragms each including a pressure sensor associated therewith, each pressure sensor configured to detect changes in pressure within a respective fluid-filled diaphragm and communicate the changes in pressure to the sensor pad which, in turn, provides feedback to the user.

21. The surgical device for providing haptic feedback according to claim 20 wherein the fluid-filled diaphragm includes hydraulic fluid.

22. The surgical device for providing haptic feedback according to claim 20 wherein the sensor pad includes an array of haptic-like sensors disposed thereon.

23. The surgical device for providing haptic feedback according to claim 20 wherein the cavity is defined by a pair of opposing C-shaped flanges.

24. The surgical device for providing haptic feedback according to claim 23 wherein the sensor pad includes an array of haptic-like sensors disposed on an inner facing surface of one of the C-shaped flanges.

* * * * *